United States Patent
Ji et al.

(10) Patent No.: US 6,726,935 B2
(45) Date of Patent: Apr. 27, 2004

(54) PHARMACEUTICAL COMPOSITION FOR PREVENTING AND TREATING ERECTILE IMPOTENCE USING PURIFIED SUMSOO EXTRACT

(75) Inventors: Joon Whan Ji, Sungnam-shi (KR); Jae Ku Kang, Kwachon-shi (KR); Young Hoon Kim, Seoul (KR); Sung Hak Jung, Seoul (KR); Hee Jae Cho, Sungnam-shi (KR); Kwang Hyuk Lee, Sungnam-shi (KR)

(73) Assignee: Cheil Jedang Corporation (KR)

( * ) Notice: Subject to any disclaimer, the term of this patent is extended or adjusted under 35 U.S.C. 154(b) by 0 days.

(21) Appl. No.: 10/168,596
(22) PCT Filed: Dec. 22, 2000
(86) PCT No.: PCT/KR00/01512
§ 371 (c)(1),
(2), (4) Date: Jun. 24, 2002
(87) PCT Pub. No.: WO01/47539
PCT Pub. Date: Jul. 5, 2001

(65) Prior Publication Data
US 2003/0003158 A1 Jan. 2, 2003

(30) Foreign Application Priority Data
Dec. 24, 1999 (KR) ............................................. 99-62052

(51) Int. Cl.⁷ ...................... A61K 35/78; A61K 35/24; A61K 35/37
(52) U.S. Cl. ...................... 424/537; 424/520; 424/522; 424/550; 424/562
(58) Field of Search ................................ 424/537, 562, 424/520, 550, 522

(56) References Cited

U.S. PATENT DOCUMENTS 5,587,167 A * 12/1996 Choi et al. .................. 424/728

FOREIGN PATENT DOCUMENTS

JP       77044366       * 11/1977

OTHER PUBLICATIONS

Derwent Abstract 1975–02039W Kyushin Seiyaku KK JP 77044366 Nov. 8, 1977.*

* cited by examiner

Primary Examiner—Herbert J. Lilling
(74) Attorney, Agent, or Firm—Cantor Colburn LLP

(57) ABSTRACT

A pharmaceutical composition for prevention or treatment of premature ejaculation and/or hypersensitivity of sexual stimulation is provided, which contains a therapeutically effective amount of a purified essence of Bufonis venenum for prevention or treatment of dysspermia or the symptom of non-controlled ejaculation in male, due to premature ejaculation and/or hypersensitivity of sexual stimulation. The Bufonis venenum may be a purified essence of Bufonis venenum extracted by use of one or more organic solvent selected from a group consisting of ethyl acetate, dichloromethane or chloroform, and concentrated, and is purified and fractionated by use of silica gel column. The composition may be formulated in a pharmaccutically acceptable formulation of ointment, suspension, gel, spray, patch or solution.

4 Claims, 3 Drawing Sheets

Lane 1: serotonin

Lane 2: epinephrine

Lane 3: 70% ethanol extract of Bufonis veneum

Lane 4: purified essence of Bufonis veneum

* Contraction % to phenylephrine(5X10⁻⁶ M) induced contraction(100%)

A: Cream-type dosage form containing ethanol extract of Bufonis veneum
B: Cream-type dosage form containing the purified essence of Bufonis veneum
C: Cream-type dosage form containing the base material
D: Phentolamine + Cream-type dosage form containing ethanol extract of Bufonis veneum

PHARMACEUTICAL COMPOSITION FOR PREVENTING AND TREATING ERECTILE IMPOTENCE USING PURIFIED SUMSOO EXTRACT

CROSS-REFERENCE TO RELATED APPLICATION

This application is the U.S. national stage of PCT Application No. PCT/KR00/01512 which has an international filing date of Dec. 22, 2000 and which was published in the English language. The present application incorporates herein by reference and claims the benefit of PCT Application No. PCT/KR00/01512.

TECHNICAL FIELD

The present invention relates to a pharmaceutical composition for prevention and/or treatment of premature ejaculation and/or hypersensitivity of sexual stimulation, more particularly to the pharmaceutical composition containing a purified essence of Sumsoo (Bufonis venenum) for prevention and/or treatment of dysspermia or the symptom of non-controlled ejaculation in male, due to premature ejaculation and/or hypersensitivity of sexual stimulation.

BACKGROUND

In general, a hypersensitivity of sexual stimulation has been known as being caused by the failure or disorder of the complicated cooperation between the peripheral and central nerve system. In particular, the term "hypersensitivity of sexual stimulation" denotes a symptom that when a man has a sexual intercourse with a woman, he ejaculates immediately before or after his penis is introduced into the virginal speculum of the woman, or even cannot control his penis to keep the erection state and/or the ejaculation for a sufficient time period for providing the woman with a sexual satisfaction, in the majority cases of their sexual intercourse.

According to the recent statistical report in Korea, approximately 30 to 50% of adult men have been troubled with such unsatisfactory sexual ability resulted from the sexual hypersensitivity. Therefore, it has become a social problem due to the friction between a husband and wife and a loss of confidence and/or the resulted enervation.

The various causes of the symptom of sexual hypersensitivity have been reported, such as a functional reduction of central nerve due to the fatigue of neuro-transmitter system, a hypersensitive response of the urinary duct or the galns receptor, the endocrinal problem, the mental cause and so forth. However, it was recently deduced that since the above-mentioned causes may react on the nerve system in simultaneous and complex manner, or a cooperation system between the central sexual nerve system in a man may be disrupted, a reflective ejaculation can easily be caused.

RELATED ART

A therapy of the symptom of sexual hypersensitivity may be classified as a mental therapy and a medicinal therapy. The mental therapy may be used to overcome the problem through the training a sexual technique for a long term with the conversation and cooperation among a physician, the patient and his sex partner. However, since this method requires a long term and a complicated process for treatment, a high amount of cost for the therapy, and an effect of circumstance such as the additional stress from outside, and a maintenance of the cooperation system is difficult for those reasons, the patients do not prefer the method due to the possible failure of treatment or the re-occurrence of the symptom. In particular, it is reported that the therapy merely results in not more than approximately 50% of success.

In practice, since the medicinal therapy is known as being more effective than the mental therapy in an aspect of the level and immediateness of the resulting effect, it is widely used for purpose of treatment of the symptom. A drug or agent used in the medicament therapy includes a psychotropic agent such as antidepressant suppressing an excitation of the central sexual nerves, and a topical anesthetic, which can delay the ejaculation time point by making the peripheral sexual nerve less sensitive. However, in case of central nerve-suppressing agent, a sexual intercourse itself may be impossible due to the loss of sexual desire, while in case of peripheral nerve-suppressing agent, a effective term of a topical anesthetic such as Lidocaine ointment or spray is so short that it must be used immediately before the sexual intercourse. In this connection, those agents could not provide a successful solution for treatment of sexual hypersensitivity.

Therefore, the various research and studies have been made to develop a successful agent for treatment of sexual hypersensitivity, and a scientific approach and the severe efforts are also made for providing a useful therapeutic method to be accepted as an excellent agent in the medical field.

A typical formulation of pharmaceutical agent has been disclosed in the trademark of SS Cream (KR Patent 0148511 owned by the applicant), whose effect has been verified as being the successful therapeutic agent for treating sexual hypersensitivity. It was a medicine for external application prepared by using nine kinds of herb extracts as the main components, such as Ginseng, Dang-gui, Sasangja, Sancho (Chinese Pepper), Yuk-Jong-Yong, Cinnamon, Sesin, Clove (Jeong-Hyang) and Bufonis venenum, which can prevent the hypersensitivity of sexual nerve by their own topical anesthetic effect.

However, as a result of search for the effect of the said formulation among the consumers who have ever used SS Cream, most of them complained of a topical fever, a pain, impotency and so forth. Furthermore, the smell from the herb components was so strong that they could not continuously use the product.

The present inventors have studied and tested intensively and extensively in order to overcome those problems, and found out that the component of Bufonis venenum, which is an ingredient secreted from the venom gland of toad, was the main component providing the side effects as well as the effect of treating the hypersensitivity of sexual nerve; and therefore, even if the component of Bufonis venenum were solely contained as the active component in a properly purified from, with extruding the other components from the therapeutic agent, the therapeutic effect of the hypersensitivity of sexual nerve being equivalent to the prior art can be maintained without the side effects caused by Bufonis venenum. On the basis of these, the inventors completed the present invention.

SUMMARY OF THE INVENTION

The present invention provides a pharmaceutical composition for treatment and prevention of the hypersensitivity of sexual nerve in male.

According to a teaching of the old Chinese pharmaceutical recipes, Bufonis venenum is secreted from the venom gland of toad, has the pharmacological effects of cardiotonic, tonic, urination, alleviation, detoxification and so forth, and is an effective component of medicine for treating premature ejaculation by topical application as well as throatache, toothache and detoxification.

However, Bufonis venenum is a kind of violent poison, and a certain cases of poisoning due to wrong or incorrect use has occasionally been reported. Therefore, the various methods had been proposed in order to reduce such violent poison. In the prior art, especially in case of SS Cream, many kinds of herb extract components seemed to have been added in order to reduce such violent poison, resulting in the problem of a unique and strong smell.

In this regard, the object of the present invention was accomplished by providing a method for purification and isolation/separation of the pharmacological component effective for treatment of premature ejaculation and/or hypersensitivity of sexual stimulation and extrude the toxic components presenting a symptom of pain; and a recipe or use including a dose and a route of administration.

Bufonis venenum used in the present invention for prevention or treatment of premature ejaculation and/or hypersensitivity of sexual stimulation may be a purified essence, which was extracted by using one or more organic solvent selected from a group consisting of ethyl acetate, dichloremethane and chloroform, and concentrated. The said purified essence of Bufonis venenum may be one which was purified and fractionated by using silica gel column.

Also, the pharmaceutical composition for prevention or treatment of premature ejaculation and/or hypersensitivity of sexual stimulation according to the present invention is not limited in the form of product, if it can be formulated for using in the topical administration. Specifically, the product of the invention can be in the various medicinal form, such as ointment, suspension, gel, spray, patch or solution.

BRIEF DESCRIPTION OF DRAWINGS

Hereinafter, the present invention is more specifically described by referring to the attached drawings.

DESTAILED DESCRIPTION OF THE INVENTION

Figure 1:
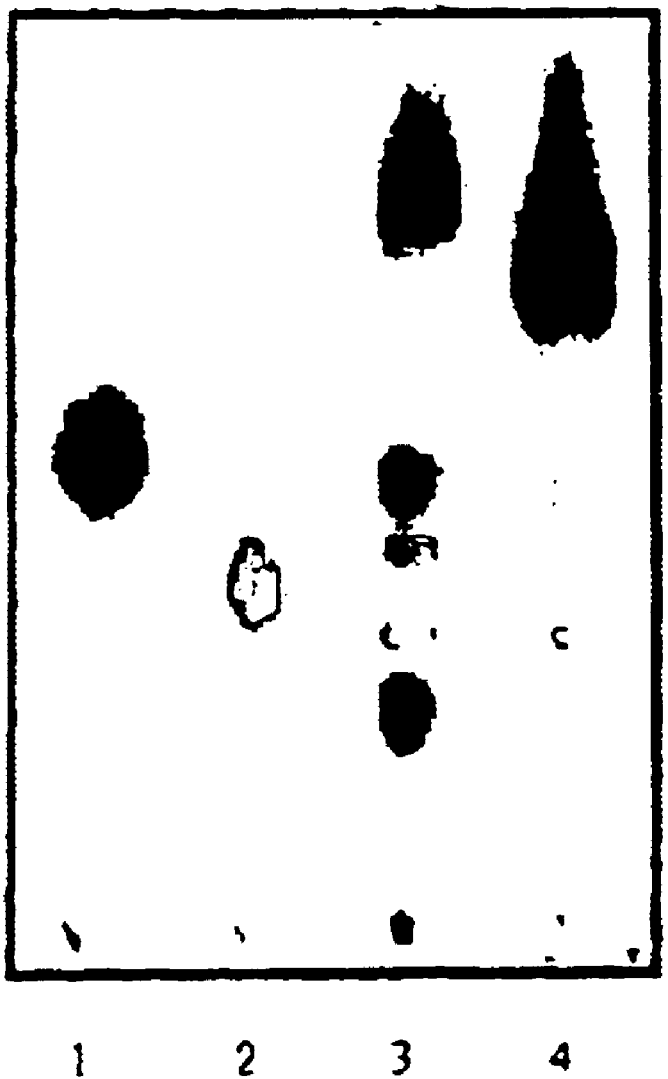
FIG. 1 depicts a result of thin layer chromatography by using the essence of Bufonis venenum.

The present invention provides a pharmaceutical composition for treatment and prevention of the hypersensitivity of sexual nerve in male.

Specifically, according to an aspect of the invention, a pharmaceutical composition for prevention or treatment of premature ejaculation and/or hypersensitivity of sexual stimulation is provided, which contains a therapeutically effective amount of a purified essence of Bufonis venenum for prevention or treatment of dysspermia or the symptom of non-controlled ejaculation in male, due to premature ejaculation and/or hypersensitivity of sexual stimulation.

In another aspect of the invention, the said Bufonis venenum is a purified essence of Bufonis venenum extracted by use of one or more organic solvent selected from a group consisting of ethyl acetate, dichloromethane or chloroform, and concentrated.

Even in another aspect of the invention, the said purified essence of Bufonis venenum is purified and fractionated by use of silica gel column.

According to further aspect of the invention, the said composition is formulated in a pharmaceutically acceptable formulation of ointment, suspension, gel, spray, patch or solution.

Bufonis venenum is a black-colored material secreted from the venom gland located in under ears and skin of toad. The pharmaceutical composition of the present invention includes the purified essence of Bufonis venenum extracted from the secreted material, purified and concentrated, as the effective ingredient.

Epinephrine contained in Bufonis venenum from toad in a certain level (app. 5%) results in the contraction of smooth muscle and cause a pain. Indol alkylamines such as Bufotenine and serotonine and so forth are also the neurotransmitters inducing the constraction of smooth muscle. Therefore, if these materials were applied in the treatment of hypersensitivity of sexual nerve in a conventional manner, the problem indicated in the prior art will still remain without solution.

Therefore, according to the invention, the purified essence of Bufonis venenum extracted from toad can be obtained, and a pharmaceutically proper dose can be added during the process, to be formulated into the final form of pharmaceuticals, such as ointment, suspension, gel, liquid, dispersion, cream, lotion, spray, patch, cataplasma and so forth.

According to Korean Patent No. 148511, Bufonis venenum were dipped into 70% warm ethanol at 50° C. for about 4 hours, and filtrated/concentrated into the purified product. By use of this process, however, the problematic material having the side effects may be extracted. In this regard, either the purified essence of Bufonis venenum by using ethyl acetate as solvent, or the fraction partially purified by use of silica column was used as the main component. The purified essence of Bufonis venenum can be homogeneously mixed with the pharmaceutically acceptable carrier to provide the therapeutic agent according to the present invention.

Although the pharmacological mechanism and effects have not completely been verified yet in the field of art, it is deduced that a cavernosal smooth muscle relaxation effect can be accomplished, Bufadienolides as the main component of the purified essence of Bufonis venenum may reduce or anesthetize the hypersensitive sensual function of the glans, which is a receptor nerve section of the reflective ejaculation nerve, the venenum can block the transmission reaction of nerve to the central nerve system to suppress the ejaculation center and to put the reflective nerve of ejaculation away from the skin as the sexual touches being made, thereby to prevent from the hypersensitive sexual stimulation, and delay the ejaculation time point.

The purified essence of Bufonis venenum contained in the pharmaceutical composition for treatment and prevention of the hypersensitivity of sexual nerve according to the present invention is preferably administrated in the topical application or massage to the skin of glans, preferably 10 minutes to 10 hours before the sexual intercourse. Specifically, when the purified essence was extracted by use of ethyl acetate, 0.2 to 10 mg of dose may preferably be applied to the hypersensitive site. Also, when it was a fraction extracted by use of silica column, 0.05 to 2 mg of dose may be preferable. In both cases, the essence must be washed out 2 to 30 minutes after application, and the effect can be kept for 8 to 12 hours.

Hereinafter, the more detailed description on the specific effect of the present invention will be given by the following Examples and Experimental Examples, without limiting the spirit and scope of the invention.

EXAMPLES

Example 1

50 g of Bufonis venenum was added into 500 ml of ethylacetate, and the mixture was stored at 60° C. for 2 hours. After storage, the mixture was filtered and the filtrate was distilled to remove ethylacetate. 500 ml of ethylacetate was then added to the remnants, and the mixture was stored at 60° C. for 2 hours and filtered to obtain the filtrate. The former and later filtrates were mixed, concentrated at 50° C. under reduced pressure, and freeze-dried to produce 6.5 g of Bufonis veneum powder.

Example 2

50 g of Bufonis veneum was added into 500 ml of chloroform, and the mixture was stored at 60° C. for 2 hours. After storage, the mixture was filtered and the filtrate was distilled to remove chloroform. 500 ml of ethylacetate was then added to the remnants, and the mixture was stored at 60° C. for 2 hours and filtered to obtain the filtrate. The former and later filtrates were mixed, concentrated at 50° C. under reduced pressure, and freeze-dried to produce 5.65 g of Bufonis veneum powder.

Example 3

50 g of Bufonis veneum was added into 500 ml of dichlomethane, and the mixture was stored at 60° C. for 2 hours. After storage, the mixture was filtered and the filtrate was distilled to remove dichlomethane. 500 ml of ethylacetate was then added to the remnants, and the mixture was stored at 60° C. for 2 hours and filtered to obtain the filtrate. The former and later filtrates were mixed, concentrated at 50° C. under reduced pressure, and freeze-dried to produce 5.35 g of Bufonis veneum powder.

Example 4

4 g of essence of Bufonis veneum extracted from example 1 was passed through the column packed with 80 g of silica gel having 240 to 400 meshes, and placed in a moving phase solvent consisting of ether and ethylacetate in a mole ratio of 3:2. The eluent was separated by thin layer chromatography and the fractions containing bufalin, cinobufogenin, or resibufogenin were only collected. The fractions were concentrated under reduced pressure to produce 847 mg of Bufonis veneum powder.

Example 5

Production of Cream-Type Dosage Form

The Bufonis veneum powder produced from example 1 was equally mixed with the base material in a weight ratio of 10 mg Bufonis veneum powder per 1 g base material to produce the colorless and odorless cream-type dosage form. The base material is a mixture of ploxamer and propyleneglycol.

The cream-type dosage form containing the Bufonis veneum powder produced by a method of Korean Patent No. 148511 and base material mixed in a weight ratio of 10 mg per 1 g was produced in order to use as a control in the following examples.

Experimental Example 1

Pain Test for the Essence of Bufonis Veneum

The pain test for rat using the extract of Bufonis veneum extracted with 70% ethanol, the purified essence of Bufonis veneum extracted by the present invention method, and the remnants solution prepared by dissolving the invention remnants in methanol was performed to identify on whether pain-causing materials in Bufonis veneum may be removed during the purification process of Bufonis veneum and the optimum condition for separating pain-causing materials.

10 $\mu$l of each 10 mg/ml testing material containing solution was hypodermically injected into the foot soles of five male rats, and then the pain occurring time was recorded at an interval of 5 minutes for 30 minutes.

These results are shown in Table 1. From these results, it is found that the purified essence of Bufonis veneum does not cause pain of rats. However, the extract of Bufonis veneum extracted with 70% ethanol contains the pain-causing materials, and the remnants solution of the invention strongly causes pain of rats. Therefore, it is suggested that the pain-causing materials is polar materials because they can be extracted by not ethylacetate but alcohol.

TABLE 1

Total pain occurring time of rats for 30 minutes after injection of each testing material

| Testing material | Total pain-causing time for 30 minutes(sec.) |
| --- | --- |
| Extract of Bufonis veneum extracted with 70% ethanol | 10.8 sec. |
| Remnants solution prepared by dissolving the invention remnants in methanol | 93.8 sec. |
| Purified essence of Bufonis veneum extracted by the present invention method | 0 |

Experimental Example 2

Thin Layer Chromatography(TLC) Analysis

In order to ascertain whether pain-causing materials such as epinephrine and serotonin in the purified essence of Bufonis veneum of the invention are removable, the ethanol extract of Bufonis veneum and the purified essence of Bufonis veneum of the invention were compared by using thin layer chromatography. 5 mg/ml of each extract was spotted on silica gel thin layer chromatography plate and developed in a development vessel saturated with a developing solution containing butanol: ethylacetate: water= 4:1:5. After development, the removal of polar materials were analyzed by spraying anisaldehyde reagents to the silica gel plate.

These results are shown in FIG. 1. In FIG. 1, it is found that the pain-causing materials are removed from the purified essence of Bufonis veneum of the invention, but they are not removed from the ethanol extract of Bufonis veneum.

Experimental Example 3

Local Anesthesia and Irritation to the Eye Mucous Membranes Analysis

In order to compare the local anesthesia effects and irritation to the eye mucous membranes of rats between the cream-type dosage form of the invention and the cream-type dosage form produced by a method of Korean Patent No. 148511 as a control, the following tests were performed.

For the test of the local anesthesia effects of each cream-type dosage form, the lower eyelid of male rabbits was pulled down and fixed. 0.1 ml of each cream-type dosage form was then administrated into the eye of male rabbits and the eye was closed for 1 minute. The eye was irritated with irritating brush 10 times at 5, 10, 20, and 30 minutes and the number of cornea response was recorded. The incomplete closing of eye or slow response was regarded as a half number.

For the test of the irritation to the eye mucous membranes of each cream-type dosage form, omission, bleeding, turbidity, dropsical swelling and eye closing of male rabbits eye administered by each cream-type dosage form were studied.

Figure 2:
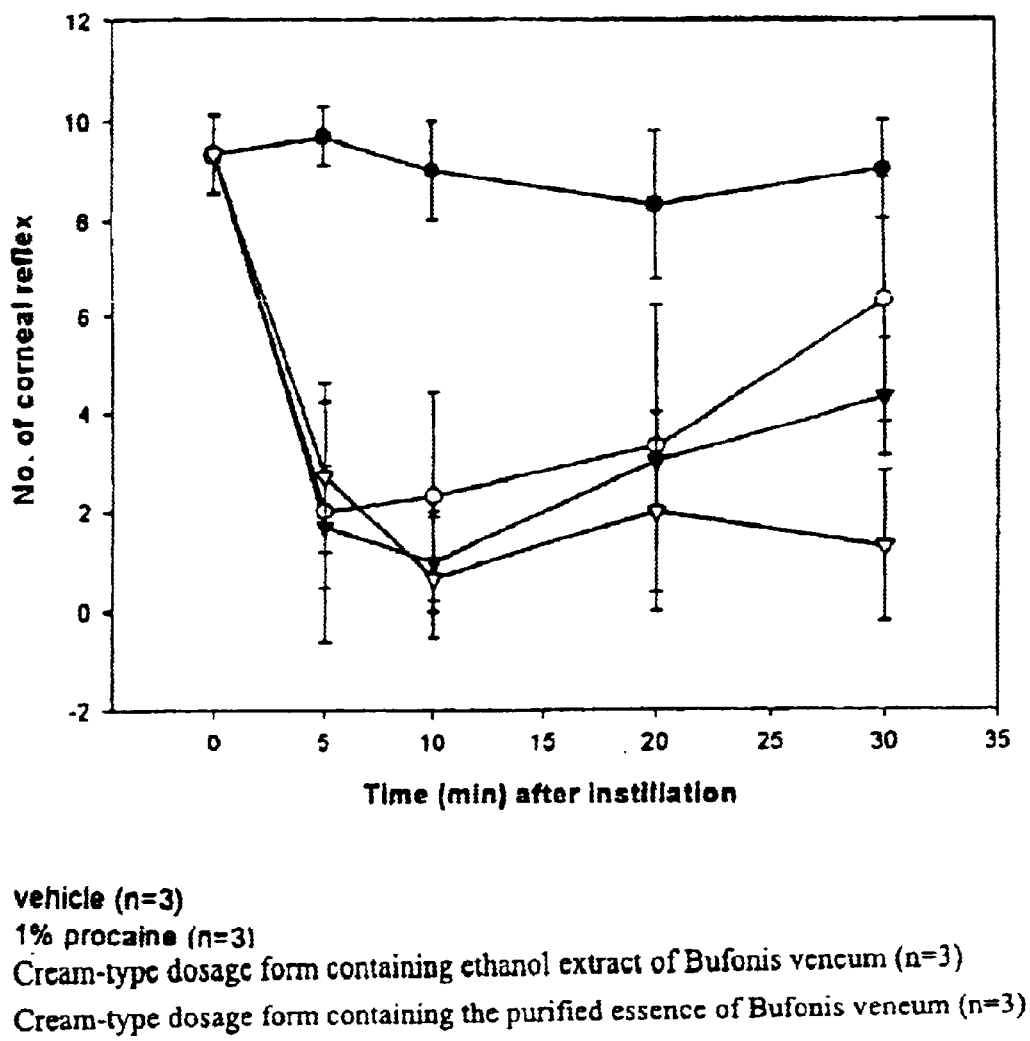
FIG. 2 depicts a result of topically anesthetizing a rabbit by using a cream containing the purified essence of Bufonis venenum.

These results are shown in FIG. 2. In FIG. 2, it is found that the cream-type dosage form of the invention has similar local anesthesia effects compared to the control cream-type dosage form, and does not irritate to the eye mucous membranes of rabbits. Therefore, it is suggested that the pain-causing materials are removed from the purified essence of Bufonis veneum, maintaining its pharmaceutical effects.

Experimental Example 4
Analysis of Response to the Contraction of Smooth Muscle in Sponge Body of Male Rabbit Penis In order to determine the response of the cream-type dosage form of the invention and the cream-type dosage form produced by a method of Korean Patent No. 148511 as a control to the contraction of smooth muscle in sponge body of male rabbit penis, the following test was performed.

A rabbit was anesthetized by intravenously injecting pentobarbital and killed. The penis of a male rabbit was extracted, dipped in a vessel containing tyroid solution, and the spongy body of penis was isolated to be used for the test. The pure spongy body tissue of penis was isolated by removing the connective tissue and surrounding muscles in the isolated spongy body of penis, and incising the tissue membrane using a surgical knife. The isolated spongy body tissue of rabbit penis was trimmed to 2×2×6 mm sized square fragment. The one end of the fragment was fixed in a vessel containing tyroid solution and the other end of the fragment was connected with a tension conversion recorder to record the contraction of the penis fragment. The temperature of tyroid solution in the vessel was maintained to 37° C. by circulating hot water through the space between double-fared wall of the vessel. The hydrogen ion concentration of tyroid solution was maintained to pH 7.4 by providing with a gas mixture mixed with 95% oxygen and 5% carbonic acid gas. The tension of the spongy body tissue at suspending period was maintained to 2 g by increasing 0.5 g of the tension each 30 minutes for 1 or 2 hours. In stable status of the spongy body tissue, its contraction was determined by administrating $5 \times 10^{-6}$M of phenylnephrine into the spongy body tissue.

Figure 3:
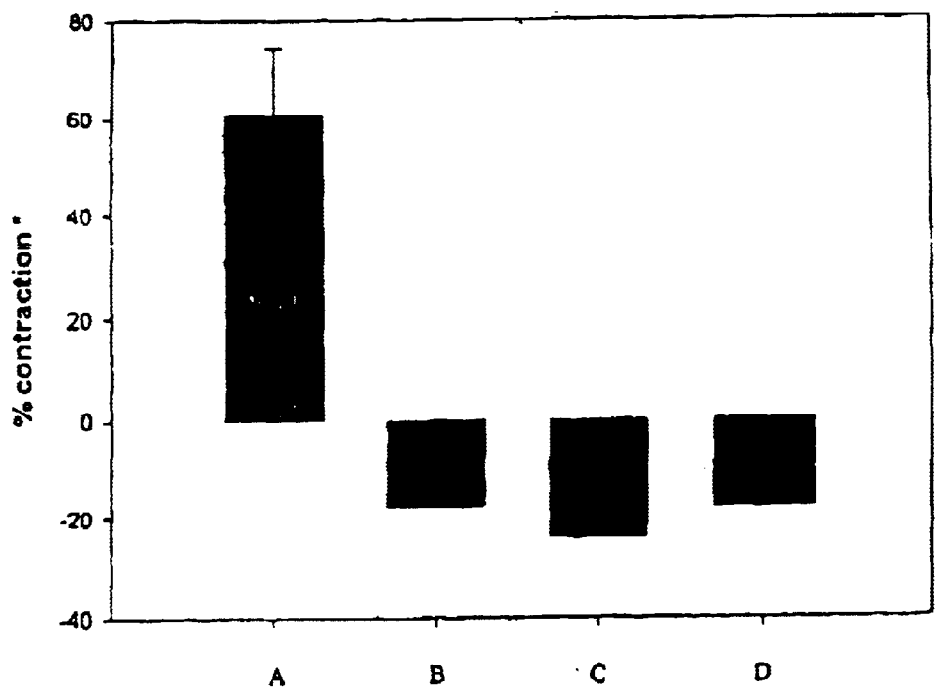
FIG. 3 depicts a result of test for the effect of the purified essence of Bufonis venenum to the contraction of penis smooth muscle of rabbit.

These results are shown in FIG. 3. As a result of these tests, 20% of relaxation was shown in the spongy body tissue administered by the base material, and 17.5% of relaxation was shown in the spongy body tissue administered by the cream-type dosage form of the invention, but 60% of contraction was shown in the spongy body tissue administrated by the control cream-type dosage form, in which the contraction causing reaction can be inhibited by pretreatment of phentolamine as a α-blocker. Therefore, it is suggested that Bufonis veneum should be purified for removing the contraction causing material such as epinephrine.

Experimental Example 5
Pain-causing Test

In order to ascertain the removal of pain caused by Bufonis veneum, 10 μl of each cream-type dosage form of example 1 and Korean Patent No. 148511 was hypodermically injected into the foot soles of five male rats, and then the pain occurring time was recorded at an interval of 5 minutes for 30 minutes. These results are shown in Table 2. As a result of Table 2, it is found that the cream-type dosage form of the invention shows no pain response, but the control cream-type dosage form shows strong pain response.

TABLE 2

| Total pain occurring time after injection of testing dosage form for 30 minutes. | |
|---|---|
| Testing materials | Total pain occurring time for 30 minutes |
| Cream-type dosage form of base material | 0 minute |
| Cream-type dosage form of Bufonis veneum | 7.3 minutes |
| Cream-type dosage form of purified essence of Bufonis veneum | 0 minute |

INDUSTRIAL APPLICABILITY

As described in the above examples and experimental examples, the pharmaceutical composition produced by a method of the present invention contains purified essence of Bufonis veneum and it is effective for the prevention or treatment of premature ejaculation and/or hypersensitivity of sexual stimulation with no side effects such as pain.

In addition, the pharmaceutical composition of the invention has prolonged effective time of medicines, so that its using time may not be limited. Therefore, the present pharmaceutical composition of the invention will contribute to the improvement of human sex life and the quality of life.

What is claimed is:

1. A pharmaceutical composition for prevention or treatment of premature ejaculation and/or hypersensitivity of sexual stimulation, which contains a therapeutically effective amount of an extract of Bufonis venenum comprising bufalin, cinobufogenin and resibufogenin, wherein epinephrine and indolalkylamines are removed.

2. The pharmaceutical composition for prevention or treatment of premature ejaculation and/or hypersensitivity of sexual stimulation according to claim 1, wherein said extract of Bufonis venenum is a purified essence of Bufonis venenum extracted by use of one or more organic solvent selected from the group consisting of ethyl acetate, dichloromethane and chloroform, and concentrated.

3. The pharmaceutical composition for prevention or treatment of premature ejaculation and/or hypersensitivity of sexual stimulation according to claim 2, wherein said purified essence of Bufonis venenum is purified and fractionated by use of silica gel column.

4. The pharmaceutical composition for prevention or treatment of premature ejaculation and/or hypersensitivity of sexual stimulation according to claim 1, wherein said composition is formulated in a pharmaceutically acceptable formulation of ointment, suspension, gel, spray, patch or solution.

* * * * *